United States Patent [19]

Cancio et al.

[11] Patent Number: 5,143,774
[45] Date of Patent: Sep. 1, 1992

[54] NONWOVEN FIBROUS EMBOSSED PLASTIC FILM

[75] Inventors: Leopoldo Cancio, Cincinnati, Ohio; Thomas C. Ryle, Burlington, Ky.; Pai-Chuan Wu, Cincinnati, Ohio

[73] Assignee: Clopay Corporation, Cincinnati, Ohio

[21] Appl. No.: 401,667

[22] Filed: Sep. 1, 1989

[51] Int. Cl.⁵ .............................................. B32B 1/00
[52] U.S. Cl. ..................................... 428/169; 428/156; 428/170; 428/171; 264/293
[58] Field of Search ............... 428/156, 170, 171, 169, 428/904; 264/293

[56] References Cited

U.S. PATENT DOCUMENTS

| | | | |
|---|---|---|---|
| 2,920,977 | 1/1960 | Adams | 428/170 |
| 3,244,571 | 4/1966 | Weisman | 428/170 |
| 3,365,353 | 5/1968 | Witman | 428/170 |
| 3,373,072 | 8/1968 | Jones | 428/170 |
| 3,484,835 | 12/1969 | Trounstine et al. | 161/130 |
| 3,507,943 | 4/1970 | Such et al. | 428/198 |
| 3,542,634 | 11/1970 | Such et al. | 428/170 |
| 4,090,007 | 5/1978 | Crowley | 428/170 |
| 4,100,324 | 7/1978 | Anderson et al. | 428/288 |
| 4,170,680 | 10/1979 | Cumbers | 428/195 |
| 4,376,147 | 3/1983 | Byrne et al. | 428/167 |
| 4,493,868 | 1/1985 | Meitner | 428/170 |
| 4,546,029 | 10/1985 | Cancio | 428/141 |

Primary Examiner—George F. Lesmes
Assistant Examiner—Beverly A. Paulikowski
Attorney, Agent, or Firm—Wood, Herron & Evans

[57] ABSTRACT

An embossed thermoplastic liquid barrier film is disclosed having a visible nonwoven fibrous three-dimensionally embossed pattern in the film on both sides. The films have thicknesses of about 0.5 to about 2 mils and an embossed depth to provide the visible nonwoven fibrous three-dimensionally embossed pattern with the film having a soft hand feel.

5 Claims, 1 Drawing Sheet

NONWOVEN FIBROUS EMBOSSED PLASTIC FILM

BACKGROUND OF THE INVENTION

Beginning several decades ago, plastic film began to achieve wide spread use in the fabrication of many useful articles, quite often as a replacement for woven fabrics. Early in the development of plastic film as a substitute for woven fabrics, patterns were created by imposing the image of a woven fabric into a film during the process of making the film. Wire screens, along with other mechanical implements, were later employed to create plastic films having various designs. As technology developed, metal rolls having engraved patterns were employed in the production of embossed plastic films which would simulate various designs. During this period of time, the person of ordinary skill in the art who made useful articles from plastic film, typically disposable diapers, covers, water repellent clothing, and the like, worked with the film on machinery and observed or studied its characteristics. Refinements or adjustments in the machinery as well as the material took place in order to produce useful articles from such embossed plastic films on high speed production machinery.

U.S. Pat. No. 3,484,835 which issued in 1969 is directed to a plastic film embossed with a pattern simulating a woven taffeta design and the film had an especially desirable characteristic of edge curl resistance during machine processing into useful articles. Embossed plastic film disclosed in this patent offered significant improvement over the earlier taffeta design which existed in the prior art. The simulated taffeta design disclosed in the above mentioned patent is only an example of many different designs created and employed by film fabricators in their effort to simulate woven fabrics or achieve other various visual appearances and physical properties which were advantageous from a manufacturing or consumer standpoint.

Another one of such many designs is referred to in the art as a matte finish. A matte finish has heretofore been characterized by a rather dull finish on a plastic film with no visually perceptible pattern. Matte finishes have been produced in films by the employment of sand-blasted embossing rollers. With the advancement of technology including new formulations in polymer compositions of the polyolefin type, particularly polyethylene, polypropylene and polybutadiene and their copolymers, the problem of handling various films has become complex. While there is a considerable amount of knowledge available to a person of skill in this art, behaviors of polymers, or their properties under various physical conditions, such as machine stress and other conditions, are not readily understood. One might say the plastic film technology is, indeed, more of an art than a science and experience has proven that problems in this area of the art are not as easily understood or solved owing to the unknown factors in handling such polymeric compositions under machine stress either in the manufacture or fabrication of such polymers into useful articles.

U.S. Pat. No. 4,376,147 which issued in 1983 is directed to an embossed thermoplastic polyolefin film simulating a matte finish having excellent winding characteristics without edge curl, extremely low gloss even on both sides and good tape adhesion values, among other advantages, theretofore unachieved in prior matte films. In contradistinction to the prior art sand-blasted matte films, the film of the U.S. Pat. No. 4,376,147 has an embossed pattern comprising embossed lines or channel-like areas which are parallel to the free lengthwise edges of the film. The embossed lines provide a generally rectangular pattern with parallel and transverse lines numbering within the range of 150 to about 300 lines per inch. Employing such an embossed pattern, the surface of the film appears to the unaided eye as a very dull surface. Up to that point in the state of the art the matte film of the mentioned patent achieved a balance of physical surface characteristics theretofore unachieved in known matte films.

More recently, issued U.S. Pat. No. 4,546,029 is directed to a random embossed thermoplastic polyolefin film simulating a matte or dull finish having excellent roll or winding characteristics and processability without edge curl. Moreover, among its other important attributes, theretofore unachieved in prior art diaper matte films, it has relatively equal tape adhesion on both sides of the random embossed film. This is an important feature in diaper films which enables diapers to be used more effectively and conveniently without tearing the film. The random pattern comprises an asymmetric arrangement of asymmetrically raised bosses and depressed areas on one side of the film, and correspondingly, underlying asymmetrically depressed areas and raised bosses on the opposite side of the film. The asymmetric bosses and depressions are of such height and area on the surfaces of both sides of the film such that the unaided eye of an observer does not detect any pattern in the film, even though it is an embossed random pattern. Such a combination of design and embossed depth had been unachieved in plastic films and, quite surprisingly, a unique balance of physical properties had been obtained.

As evidenced by the above background, production of plastic film has been a continuously improving technology and there are demands for further innovation.

SUMMARY OF THE INVENTION

This invention is directed to a nonwoven fibrous embossed plastic film. In contrast to plastic films simulating woven or matte-like finishes, the film of this invention simulates the appearance of a nonwoven fibrous web. The nonwoven fibrous embossed film of this invention provides a barrier against liquid and yet indeed provides the appearance and feel of a nonwoven fibrous web.

In one of its aspects, the nonwoven fibrous embossed plastic film provides a three-dimensional effect with a realistic visual appearance. In other words, upon inspection by an unaided eye, individual fibers appear to stand out from the surface and a nonwoven fibrous appearance is created. Yet, the film does provide a soft hand feel thereby eliminating the artificial effect otherwise attributable to plastic substrate. Accordingly, this invention provides for a new dimension in embossed plastic films after several decades of embossed film development as set forth in the background of this invention.

The visible nonwoven fibrous embossed pattern comprises on the film top side raised random fiber bosses intersecting other random fiber bosses. The bosses are raised at varying heights and have depressed areas therebetween to provide a three-dimensionally visible pattern. On the opposite film side another visible nonwoven fibrous embossed pattern is provided substantially corresponding to and underlying the film top side pattern.

The films of this invention are relatively thin, particularly on the order of about 0.5 to about 2 mils. The surface of the film is dull and has a gloss on the order of about 4 to about 7 as measured by 45° head. It has been surprisingly found that a nonwoven fibrous texture may be embossed in a plastic film to provide a three-dimensional effect and yet have a soft hand feel with a non-glossy surface. The overall embossed depth of the film will vary but will tend to be on the order of about 6 to about 10 mils for a film of about 0.5 to 2 mils thickness.

DETAILS OF THE INVENTION

The nonwoven fibrous embossed film is made from any one of a number of suitable plastic materials, preferably of the thermoplastic type and particularly polyolefins including polyethylene, polypropylene, polybutadiene and copolymers of such polyolefins such as ethylene vinyl acetate, ethylene methyl acrylate and ethylene propylene diene monomer (EPDM). These polymers may be modified with conventional fillers, stabilizers, additives and the like. These film materials are embossed to give the nonwoven fibrous appearance for a number of applications including diapers, napkins and underpad applications as well as other medical disposable articles where the nonwoven appearance is desirable.

A preferred polyolefin film is ultralow, low density or medium density polyethylene. As is understood in the art, ultralow density polyethylene has a density of 0.890-0.912 with increasing density to 0.916 to 0.935 for low density polyethylene. Linear low density polyethylene having a density of 0.918 to 0.941 is also very suitable for use in accordance with this invention. Blends of the above ultralow density polyethylene, conventional high pressure polyethylene and low pressure linear low density polyethylene may be employed. For instance, 80% ultralow density polyethylene at a density of 0.912 may be blended with 20% high pressure low density polyethylene at a density of 0.922 with a blend density of approximately 0.914. In order to achieve a soft and quiet product, the modulus, referred to as 1% secant modulus, of the formulated film may vary within the range of about 5,000 psi to 40,000 psi, with 5,000 psi to 20,000 psi preferred. A soft and quiet product is obtained with polyethylene having a modulus in the range of about 5,000 psi to 20,000 psi. A modulus in this range provides for a soft, quiet and good hand-feel diaper for instance.

The above plastic films can be embossed with the nonwoven fibrous design of this invention according to any one of a number of well-known techniques. A preferred method involves the introduction of thermoplastic material in a plastic state between a steel embossing roll and a smooth resilient roll or rubber roll which form a nip for embossing film. These techniques are considered to be conventional as described in the above mentioned patents that are embodied herein by reference.

The invention will be further understood with reference to the drawings in which.

Figure 1:
FIG. 1 is a non-magnified photographic view of the nonwoven fibrous embossed film of this invention from a top (metal embossing roll side) of the film.
Figure 3:
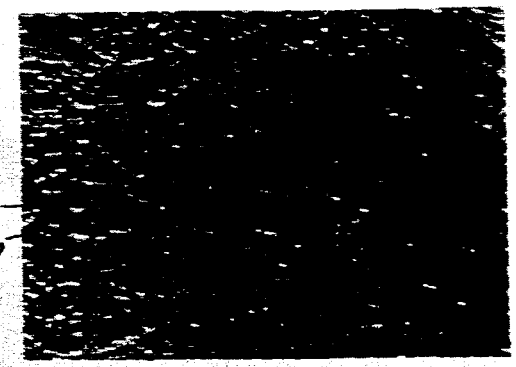
FIG. 3 is a non-magnified photographic view of another nonwoven fibrous film of this invention from a top (metal embossing roll side) of the film.
Figure 2:
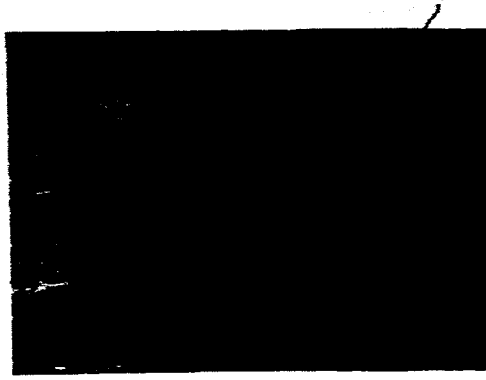
FIG. 2 is a non-magnified photographic view of the embossed film of FIG. 1 when viewed from the underside (rubber roll side) of the film.
Figure 5:
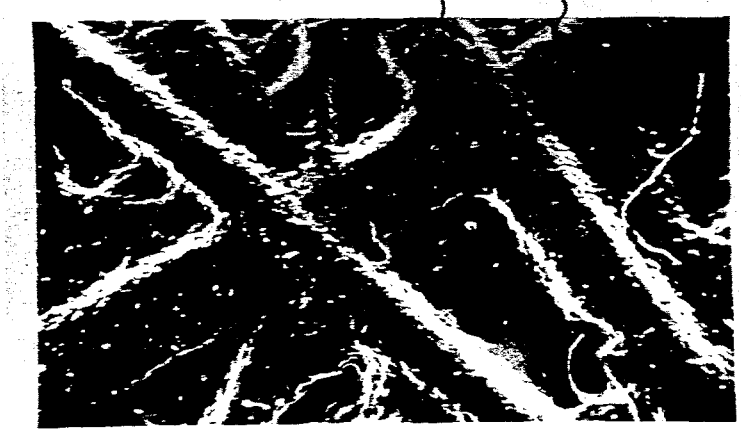
FIG. 5 is a photograph of a film like that shown in FIG. 1 on a magnified scale about 25× that shown in FIG. 1.
Figure 6:
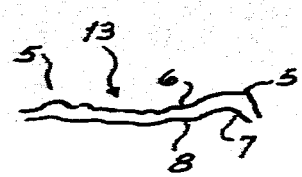
FIG. 6 is a diagramatic partial cross-section through a film like that shown in FIG. 5.

With reference to the photographs of FIGS. 1 and 3, a polyethylene film is shown in top view on the metal roll side of the film (FIG. 1) and the underside of the film (FIG. 3). With reference to the FIG. 1 top view, raised random fiber bosses 5 are shown intersecting other random fiber bosses 6 in three-dimensions with respect to one another. This is better shown in the magnified view of FIG. 5 showing the top view of a film like that shown in FIG. 1 on a magnified scale of 25×. Thus, with reference to both FIGS. 1 and 5, the bosses 5, 6 are raised at different heights and also have depressed areas therebetween in order to provide the visual appearance of a nonwoven fibrous web. The embossed continuous film still is a liquid barrier. On the underside or rubber roll side of the film, as shown in FIG. 2, the raised random fiber bosses 7 intersect raised random fiber bosses 8 to substantially underly and correspond to the visual pattern on the top side of the thinly embossed film. The photographic representations of the underside or rubber roll side of the film are not intended to correspond exactly with the photographic top or metal roll side of FIG. 1. Nevertheless, it is to be understood that in the thin films on the order of about 0.5 to about 2 mils thickness, the top side pattern of raised random fiber bosses and surrounding depressions have corresponding depressed fibers and raised fiber areas or bosses on the underside of the film. This is diagramatically shown in FIG. 6 in partial cross-section showing the relationship of top side fiber bosses 5, 6 to underside fiber bosses 7, 8. Top side bosses 5, 6 intersect and are raised at different heights and have depressed areas therebetween generally shown at 13 in FIG. 6. It should be clearly understood that FIG. 6 is diagramatic and not intended to represent the exact film structure because thin plastic film and polymers do not predictably behave when an actual slice would be made therethrough to relieve stresses in molecular structure. This will be understood by a person of skill in this art.

The nonwoven fibrous pattern is actually formed by an engraving roll having a distribution of elongated fiber depressions and raised fiber areas simulating nonwoven fibers in three-dimensional array. The process of engraving, master tooling and details thereof are not essential to this invention. With reference to the photographic magnifications of the drawing, the metal roll side of the embossing roll is mirrored in the plastic film.

Figure 4:
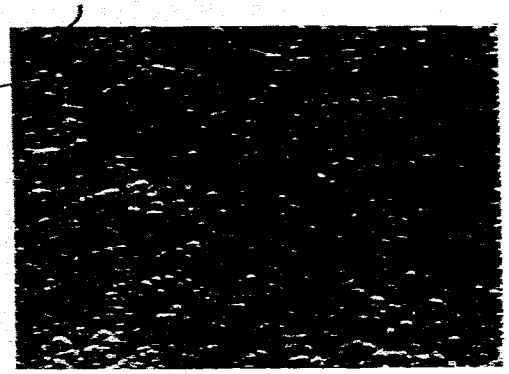
FIG. 4 is a non-magnified photographic view of the underside of the film of FIG. 3.

With respect to FIGS. 2 and 4 another embodiment of the nonwoven fibrous plastic film is shown from the top and opposite side of the thinly embossed film. The same characterization with respect to the film shown in FIGS. 1 and 3 applies to FIGS. 2 and 4 except that the embossed pattern of raised random fiber bosses 9 intersect fiber bosses 10 on the top side of FIG. 2 to provide a finer fiber visual effect in three dimensions than that of FIGS. 1 and 3 in magnified view. The opposite side as shown in FIG. 4 substantially corresponds to the top side of FIG. 2 as providing a finer nonwoven fibrous appearance raised random fiber bosses 11 intersecting fiber bosses 12. As indicated above, in order to provide a three-dimensional affect, the depth of the emboss must be sufficient to give the appearance and fiber feel. Thus, in films on the order of about 0.5 to about 2 mils in thickness, an embossed depth on the order of about 6 to about 10 mils is obtained. As demonstrated by FIGS. 1-5, the average fiber diameter may vary from about 5 to about 100 mils and may be continuous filaments or staple fibers of 1 to 3 inches in length, depending upon the nonwoven fibrous appearance that is being sought.

The "embossed depth" is determined by (a) measuring overall cross-sectional thickness of the film from the top side of the raised fiber bosses to the opposite undermost fiber ridges (or bosses) on the underside, (b) measuring or determining the average film thickness and subtracting (a) from (b). This measurement may be made in a number of manners. For instance, a standard 1 inch micrometer may be used in a manner known to those of ordinary skill in the art, to measure the embossed depth by measuring (a) and (b). For purposes of this invention, the film thickness may be calculated, based on film density. The embossed depth is the difference between the film embossed gauge as measured by a micrometer and the film thickness calculated on the basis of film density. The film embossed gauge is normally measured by a TMI Model 549M load micrometer with a 2 inch diameter anvil.

The nonwoven fibrous embossed pattern as photographically depicted as shown in FIGS. 1-4 has a number of advantages as indicated above. The pattern simulates a nonwoven fibrous fabric or cloth appearance heretofore unachieved in embossed plastic films. It has also been found that this film may be processed advantageously and employed in diaper, napkin and underpad applications as well as other medical disposable articles where a nonwoven appearance is desirable. Among its other unique features, the film has very low gloss on both sides. Films of this invention may be provided with the nonwoven appearance and still have a soft, quite and good hand-feel for these various applications.

A nonwoven fibrous embossed plastic film is formed by embossing with a system of embossing rollers as well understood at this time in the art with reference to the patents incorporated in the background of the invention. The descriptions in these patents are incorporated herein by reference so that one of ordinary skill in the art may obtain further details of embossing processes.

In a preferred form of the invention, low to medium density polyethylene, for instance, is formed into a nonwoven fibrous film by a slot-die extrusion means. For example, the low to medium density polyethylene material is heated to a temperature of about 300°-500° F. and then introduced in a web form through a slot into the nip of a steel and rubber roll system referred to above. The plastic material, upon being introduced between the nip of the rolls, is film-formed and at the same time textured with the nonwoven fibrous embossed pattern of the steel embossing roll. Under suitable embossing pressure, for instance of about 75-120 pounds per linear inch, a thin film having the embossed design may be produced. In achieving the preferred film thickness of between about 0.5 to about 2 mils, along with the necessary emboss depth of about 6 to about 10 mils, conditions are controlled in a manner well within the skill of those knowledgeable in the art of producing embossed films with the understanding of this invention. The factors which are considered may be varied depending upon the plastic material used and the characteristics to be obtained in the resultant film. Thus, process conditions that are obviously controlled to produce embossed film include temperature, pressure exerted between the nip of the embossing roll or system, the depth of the engraved design on the steel roll and the hardness of the rubber roll. Again, with reference to FIGS. 1-2, a specific nonwoven fibrous embossed film is shown and may be produced according to the above embossing technique that results in a coarse entangled fiber appearance with a surface gloss of about 4-7 as determined by a 45° head technique (ASTM Technique D-2457). The overall material thickness is on the order of about 1.2 mils with an overall depth of about 8. For a specific polyethylene film as shown by FIGS. 3-4, a finer fibrous appearance is demonstrated by the surface gloss of about 5.5 and a material thickness of about 1.2 with an overall embossed depth of about 8.

Having described the above invention in its preferred parameters, various modifications may be made as understood by a person of ordinary skill in this art in view of this specification.

What is claimed is:

1. An embossed thermoplastic liquid barrier film having a nonwoven fibrous three-dimensionally embossed pattern in the film on both sides, said film having a thickness of about 0.5 to about 2 mils and an embossed depth sufficient to provide the embossed pattern comprising, on the film top side, raised random fiber bosses intersecting other random fiber bosses, said bosses raised at different heights and having depressed areas therebetween to provide said visible pattern and on the opposite film side another visible nonwoven fibrous embossed pattern is provided substantially corresponding to and underlying said film top side pattern, said top side pattern of raised random fiber bosses and depressed areas therebetween overly respectively corresponding depressed fiber areas and raised fiber bosses on the underside of said film, said film having a soft hand feel.

2. The embossed film of claim 1 wherein said thermoplastic is selected from the group consisting of polyethylene, polypropylene and copolymers thereof.

3. The embossed film of claim 1 wherein said film has a thickness on the order of about 1 mil and an embossed depth of about 8 mils.

4. The embossed film of claim 1 wherein said thermoplastic is low to medium density polyethylene.

5. An embossed polyethylene liquid barrier diaper or pad film for disposable hygenic and surgical liquid barrier applications having a visible nonwoven fibrous three-dimensionally embossed pattern in the film on both sides, said film having a thickness of about 0.5 to about 2 mils and an embossed depth of about 6 to about 10 mils wherein the embossed pattern comprising, on the film top side raised random fiber bosses intersecting other random fiber bosses, said bosses raised at different heights and having depressed areas therebetween to provide said visible pattern and on the opposite film side another visible nonwoven fibrous embossed pattern is provided substantially corresponding to and underlying said film top side pattern, said top side pattern of raised random fiber bosses and depressed areas therebetween overly respectively corresponding depressed fiber areas and raised fiber bosses on the underside of said film, said film having a soft hand feel.

* * * * *

UNITED STATES PATENT AND TRADEMARK OFFICE
CERTIFICATE OF CORRECTION

PATENT NO.   :   5,143,774
DATED        :   September 1, 1992
INVENTOR(S)  :   Leopoldo Cancio et al It is certified that error appears in the above-identified patent and that said Letters Patent is hereby corrected as shown below:

Col. 6, lines 26-27 "film having a nonwoven" should be
--film having a visible nonwoven--

Signed and Sealed this

Nineteenth Day of October, 1993

Attest:

BRUCE LEHMAN

*Attesting Officer*    *Commissioner of Patents and Trademarks*